United States Patent
Hsieh et al.

(10) Patent No.: US 9,011,839 B2
(45) Date of Patent: Apr. 21, 2015

(54) **ANTI-INFLAMMATORY AND ANTI-VAGINITIS FOOD COMPOSITION AND PHARMACEUTICAL COMPOSITION CONTAINING *LACTOBACILLUS***

(75) Inventors: Pei-Shan Hsieh, Xinshi Township, Tainan County (TW); Yi-Chun Tsai, Xinshi Township, Tainan County (TW); Albert Kuo, Xinshi Township, Tainan County (TW); Yi-Chun Chen, Xinshi Township, Tainan County (TW)

(73) Assignee: Glac Biotech Co., Ltd., Xinshi Township, Tainan County (TW)

( * ) Notice: Subject to any disclaimer, the term of this patent is extended or adjusted under 35 U.S.C. 154(b) by 650 days.

(21) Appl. No.: 13/097,995

(22) Filed: Apr. 29, 2011

(65) Prior Publication Data

US 2011/0268715 A1 Nov. 3, 2011

(30) Foreign Application Priority Data

Apr. 30, 2010 (TW) .............................. 99113843 A

(51) Int. Cl.
*C12N 1/20* (2006.01)
*A23L 1/30* (2006.01)

(52) U.S. Cl.
CPC .............. *A61K 35/747* (2013.01); *A23L 1/3014* (2013.01); *A23V 2002/00* (2013.01); *A23Y 2220/03* (2013.01); *A23Y 2220/71* (2013.01); *A23Y 2220/73* (2013.01); *A23Y 2220/79* (2013.01)

(58) Field of Classification Search
None
See application file for complete search history.

(56) References Cited

U.S. PATENT DOCUMENTS 6,156,320 A * 12/2000 Izvekova et al. ......... 424/197.11
6,277,370 B1 * 8/2001 Cavaliere Ved. Vesely et al. ........................ 424/93.45
7,842,495 B2 * 11/2010 Yamahira et al. .......... 435/252.9

OTHER PUBLICATIONS

Meydani et al., Am J Clin Nutr 2000, 71:861 72).*
Hilton, et al., American College of Physicians, Mar. 1, 1992, vol. 116, No. 5, pp. 353-357.*
Reid et al., FEMS Immunology and Medical Microbiology 35 (2003) 131-134.*
Joint FAO/WHO Working Group Report, "Guidelines for the Evaluation of Probiotics in Food," Report of a Joint FAO/WHO Working Group on Drafting Guidelines for the Evaluation of Probiotics in Food, Apr. 30-May 1, 2002, pp. 1-11, London Ontario, Canada.
Kaewsrichan et al., "Selection and identification of anaerobic lactobacilli producing inhibitory compunds against vaginal pathogens," FEMS Immunol Med Microbiol, 2006, pp. 75-83, vol. 48.
Strus et al., "The in vitro activity of vaginal *Lactobacillus* with probiotic properties against *Candida*," Infectious Diseases in Obstetrics and Gynecology, Jun. 2005, pp. 69-75, vol. 13—No. 2.
Atassi et al., "*Lactobacillus* strains isolated from the vaginal microbiota of healty women inhibit *Prevotella bivia* and *Gardnerella vaginalis* in coculture and cell culture," FEMS Immunol Med Microbiol, 2006, pp. 424-432, vol. 48.
Shalev et al. "Ingestion of Yogurt Containing *Lactobacillus acidophilus* Compared with Pasteurized Yogurt as Prophylaxis for Recurrent Candidal Vaginitis and Bacterial Vaginosis," Arch Fam Med, 1996, pp. 593-596, vol. 5.
Barrons et al., "Use of *Lactobacillus* Probiotics for Bacterial Genitourinary Infections in Women: A Review," Clinical Therapeutics, 2008, pp. 453-468, vol. 30—No. 3.
Falagas et al., "Probiotics for the treatment of women with bacterial vaginosis," Clinical Microbiology and Infection, Jul. 2007, pp. 657-664, vol. 13—No. 7.

* cited by examiner

*Primary Examiner* — Irene Marx
(74) *Attorney, Agent, or Firm* — Muncy, Geissler, Olds & Lowe, P.C.

(57) ABSTRACT

An anti-inflammatory and anti-vaginitis food composition and/or pharmaceutical composition includes *Lactobacillus salivarius* subsp. *salicinius* AP-32 (CCTCC stock No. M2011127), *Lactobacillus reuteri* TE-33 (CCTCC stock No. M2011126), *Lactobacillus acidophilus* F-1 (CCTCC stock No. M2011124), *Lactobacillus rhamnosus* CT-53 (CCTCC stock No. M2011129) or combinations thereof. The present invention may inhibit TNF-α secretion and promote IL-10 secretion of dendritic cells and therefore inhibit inflammation, particularly inflammation of vagina mucosa cells. The present invention may be presented as oral probiotics and direct-use vagina probiotics.

11 Claims, 2 Drawing Sheets

ANTI-INFLAMMATORY AND ANTI-VAGINITIS FOOD COMPOSITION AND PHARMACEUTICAL COMPOSITION CONTAINING *LACTOBACILLUS*

BACKGROUND OF THE INVENTION

1. Field of the Invention

The present invention relates to a food composition and pharmaceutical composition, particularly to a food composition and pharmaceutical composition containing *Lactobacillus* and used for anti-inflammation.

2. Description of the Prior Art

Probiotics, according to the internationally published literature, are now defined as active microorganisms that are capable of promoting host health. Probiotics have been identified for promoting human health since end of last century with subsequent preceding research for scientific validation. Probiotics were first identified with capabilities in mitigating gastrointestinal upset symptoms, and till now, gastrointestinal moderation is still one of most important applications for probiotic products.

However, in addition to applications in gastrointestinal tracts, applications of probiotics in immune modulation have started to emerge in recent years and have been proven with booming literature and research related to probiotics and immune modulation. There are many ongoing research topics of probiotics applied in immunity, such as immunity enhancement, allergy modulation, mitigation in auto-immune diseases, anti-inflammation and so on. Ordinary oral LAB (lactic acid bacteria) products may only be provided with gastrointestinal modulation for health, and despite of thousands of natural existing LAB strains, only few of them are provided with characteristics in immune modulation or even anti-inflammation. Only few LAB strains have been identified and proven with immune modulation till now. LAB strains that are provided with special effects for human health are called functional probiotics, and are determined based on specific strains instead of species. (Guidelines for the evaluation of probiotics in food; Report of joint FAO/WHO working group on drafting guidelines for the evaluation of probiotics in food; London Ontario, Canada April 30 and May 1, 2002: 1-7)

Anti-inflammatory probiotics may contribute for alleviating vaginitis, particularly via oral route of administration to achieve accelerated vaginitis mitigation. There have been many domestic and international literatures reporting probiotics used for anti-vaginitis. As for in vitro assay, Kaewsrichan et al. (2006) reported that *Lactobacillus crispatus* and *Lactobacillus jensenii* are found to secret $H_2O_2$ and bacteriostatic compounds for suppressing and eliminating pathogenic bacteria in the vagina. Strus et al. (2005) reported that growth of vaginal candidiasis is found to be suppressed after co-culture with *Lactobacillus acidophilus, Lactobacillus rhamnosus, Lactobacillus plantarum* and *Lactobacillus fermentum*. Atassi et al. (2006) reported that *Lactobacillus gasseri* is added to a co-culture system where cells are adhered by pathogenic strains by co-culture of HeLa cells (simulating vaginal mucosa endothelial cells) with pathogenic strains for vaginitis, *Gardnerella vaginalis* and *Prevotella bivia* and it is found that the adherence of *Gardnerella vaginalis* and *Prevotella bivia* to HeLa cells is blocked by *Lactobacillus gasseri*, particularly at pH=4.5-5.5. It shows that the existence of probiotics contributes to the suppression and elimination of pathogenic strains causing vaginitis and maintenance of mild acid vaginal mucosa, which is resulted in a stimulating factor for suppressing pathogenic strains and activating probiotics. The above-mentioned literatures have proven that probiotics are capable of counteracting pathogenic strains for vaginitis to improve vaginitis symptoms.

As for clinical trials for LAB, Shalve et al. (1996) reported that the 60% of vaginitis patients, in contrast to 25% for placebo, revealed improvement after taking yogurt containing $10^8$×*Lactobacillus acidophilus* for 2 months. Barrons et al (2008) reported that 88% of vaginitis patients, in contrast to 38% for acetic acid, revealed improvement after treated with tampons immersed with yogurt containing *Lactobacillus acidophilus* and 5% acetic acid for 4-8 weeks. Falagas et al. (2007) reported that 87.5% of vaginitis patients revealed improvement after taking a capsule containing *Lactobacillus rhamnosus* and *Lactobacillus fermentum* ($>10^9$) each day for 60 days.

However, only few LAB strains are resistant to acid and bile salt and provided with capability of adherence to mucosa endothelial cells and viability through gastrointestinal tract and it is necessary to screen for functional probiotics promoting health.

To sum up, it is now a current goal to identify suitable LAB for functional probiotics that are capable of anti-inflammation, particularly to anti-vaginitis.

SUMMARY OF THE INVENTION

The present invention is directed to a food composition and pharmaceutical composition, which can inhibit TNF-α secretion and promote IL-10 secretion so as to inhibit inflammation response.

The present invention is also directed to a food composition and pharmaceutical composition, which is provided with resistance to acid and bile salt and can be applied as oral probiotics.

In addition, the present invention is directed to a food composition and pharmaceutical composition, which is provided with resistance to anti-vaginitis suppositories and can be applied for treating vaginitis.

In one embodiment, a food composition of the present invention applied for anti-inflammation includes at least one *Lactobacillus* strain and a physiologically acceptable excipient or diluent. The *Lactobacillus* strain includes *Lactobacillus salivarius* subsp. *salicinius* AP-32 (CCTCC stock No. M2011127), *Lactobacillus reuteri* TE-33 (CCTCC stock No. M2011126), *Lactobacillus acidophilus* F-1 (CCTCC stock No. M2011124), *Lactobacillus rhamnosus* CT-53 (CCTCC stock No. M2011129) or combinations thereof.

In another embodiment, a pharmaceutical composition of the present invention applied for anti-inflammation includes at least one *Lactobacillus* strain and a pharmaceutically acceptable excipient or diluent. The *Lactobacillus* strain includes *Lactobacillus salivarius* subsp. *salicinius* AP-32 (CCTCC stock No. M2011127), *Lactobacillus reuteri* TE-33 (CCTCC stock No. M2011126), *Lactobacillus acidophilus* F-1 (CCTCC stock No. M2011124), *Lactobacillus rhamnosus* CT-53 (CCTCC stock No. M2011129) or combinations thereof.

Other advantages of the present invention will become apparent from the following descriptions taken in conjunction with the accompanying drawings wherein certain embodiments of the present invention are set forth by way of illustration and examples.

BRIEF DESCRIPTION OF THE DRAWINGS

The foregoing aspects and many of the accompanying advantages of this invention will become more readily appreciated as the same becomes better understood by reference to the following detailed descriptions, when taken in conjunction with the accompanying drawings, wherein.

DESCRIPTION OF THE PREFERRED EMBODIMENT

Figure 1:
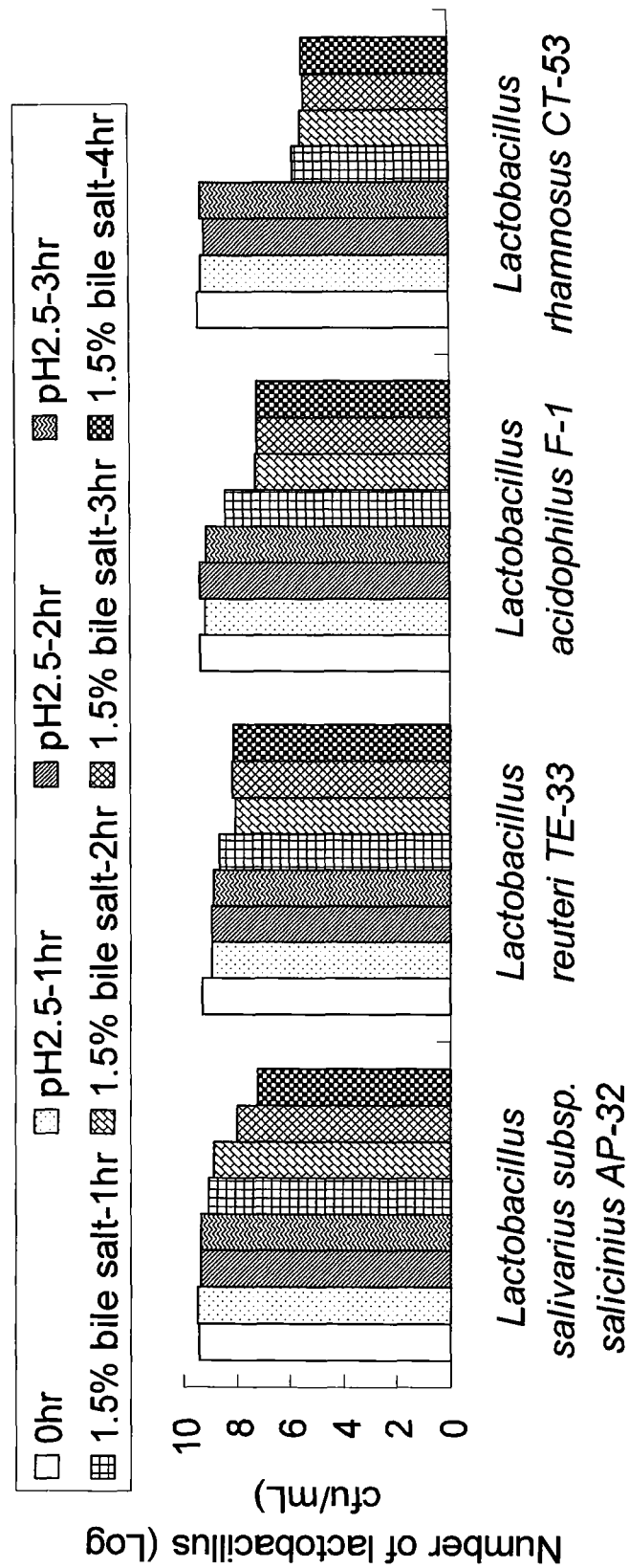
FIG. 1 is a block diagram schematically illustrating resistance of *Lactobacillus salivarius* subsp. *salicinius* AP-32, *Lactobacillus reuteri* TE-33, *Lactobacillus acidophilus* F-1 and all of *Lactobacillus rhamnosus* CT-53 to gastric acid and bile salt, where *Lactobacillus salivarius* subsp. *salicinius* AP-32, *Lactobacillus reuteri* TE-33, *Lactobacillus acidophilus* F-1 and *Lactobacillus rhamnosus* CT-53 are not affected by gastric acid; as for bile salt, *Lactobacillus rhamnosus* CT-53 is sensitive to bile salt while *Lactobacillus salivarius* subsp. *salicinius* AP-32, *Lactobacillus reuteri* TE-33 and *Lactobacillus acidophilus* F-1 are not affected; therefore, the anti-vaginitis *Lactobacillus* strains of the present invention are able to overcome obstacles within human digesting system.

The present invention is generally directed to food composition or pharmaceutical composition comprising at least one *Lactobacillus* strain including *Lactobacillus salivarius* subsp. *salicinius* AP-32 (CCTCC stock No. M2011127), *Lactobacillus reuteri* TE-33 (CCTCC stock No. M2011126), *Lactobacillus acidophilus* F-1 (CCTCC stock No. M2011124), *Lactobacillus rhamnosus* CT-53 (CCTCC stock No. M2011129) or combinations thereof; and biologically acceptable excipient or diluent. Here the *Lactobacillus* strains may be active or inactivated strains, and the food composition includes without limitation to fermented milk, yogurt, cheese, milk beverage powder, tea, coffee or combinations thereof.

The pharmaceutical composition may include oral formulations, such as tablets, capsules, potion, powder and so on; and topical formulations, such as ointment, spray, gel, powder or cream.

In addition, the present invention may be applied for anti-vaginitis and applied as feminine hygiene products including without limitations to spray, ointment or tampon.

Morphology and General Properties of *Lactobacillus* Strains of the Present Invention The lyophilized culture of the above-mentioned strains of the present invention has been deposited in China Typical Culture Collection Center (Wuhan University, China. Wuhan 430072) on Apr. 10, 2011. Deposition information is detailed in Table 1. The deposited material has been accepted for deposit under Budapest Treaty on the international Recognition of the Deposit of Microorganisms for the purpose of Patent Procedure, and all restrictions on the availability to the public of the material so deposited will be irrevocably removed upon the granting of a patent.

TABLE 1

Name and deposition information of LAB

| No. | Genre | Deposition No. |
|---|---|---|
| AP-32 | *Lactobacillus salivarius* subsp. *salicinius* | CCTCC M2011127 |
| TE-33 | *Lactobacillus reuteri* | CCTCC M2011126 |
| F-1 | *Lactobacillus acidophilus* | CCTCC M2011124 |
| CT-53 | *Lactobacillus rhamnosus* | CCTCC M2011129 |

The taxonomical characteristics of those strains have been confirmed with analysis result obtained from 16S rDNA sequence analysis and API bacterial identification system.

According to the results, strain No. AP-32 has been identified as *Lactobacillus salivarius* subsp. *salicinius*, TE-33 has been identified as *Lactobacillus reuteri*, F-1 has been identified as *Lactobacillus acidophilus* and CT-53 has been identified as *Lactobacillus rhamnosus*.

Morphology and general properties of these *Lactobacillus* strains are detailed in Table 2.

TABLE 2

Morphology and general properties of these *Lactobacillus* strains

| Strain Name | Morphology and general properties |
|---|---|
| *Lactobacillus salivarius* subsp. *salicinius* AP-32 | 1. Morphology: rod-like shape, round shape at two end, cocci in single, pairs or short chains in MRS medium.<br>2. Gram positive microorganisms, non-sporing, catalase (-), peroxidase(-), non-motile; facultative microorganisms with heterofermentative metabolism having no gas production from glucose metabolism, with optimized growth temperature = 37 ± 1° C. |
| *Lactobacillus reuteri* TE-33 | 1. Morphology: rod-like shape, round shape at two end, cocci in single, pairs or short chains in MRS medium.<br>2. Gram positive microorganisms, non-sporing, catalase (-), peroxidase(-), non-motile; facultative microorganisms with heterofermentative metabolism having no gas production from glucose metabolism, with optimized growth temperature = 37 ± 1° C. |
| *Lactobacillus acidophilus* F-1 | 1. Morphology: short or bigger rod-like shape, square shape at two end, cocci in single, pairs or short chains in MRS medium.<br>2. Gram positive microorganisms, non-sporing, catalase (-), peroxidase(-), non-motile; facultative microorganisms with heterofermentative metabolism having no gas production from glucose metabolism, with optimized growth temperature = 37 ± 1° C. |
| *Lactobacillus rhamnosus* CT-53 | 1. Morphology: short or bigger rod-like shape, square shape at two end, cocci in single, pairs or short chains in MRS medium.<br>2. Gram positive microorganisms, non-sporing, catalase (-), peroxidase(-), non-motile; facultative microorganisms with heterofermentative metabolism having no gas production from glucose metabolism, with optimized growth temperature = 37 ± 1° C. |

Anti-Inflammation Test

It has been known that in a Th17-induced inflammatory response, Th17, a kind of helper T cells, are simulated by TNF-α (tumor necrosis factor-α) and secret a number of cytokines, e.g. IL-6 and IL-17 and intermediates to induce aggregation of inflammatory cells in combination to cause inflammatory response of infection. In addition, it has been found IL-10 is provided with capability in anti-inflammation by inhibiting the generation of inflammatory cytokines such as IL-6 and TNF-α. Therefore, the inflammatory condition caused by over-reacting Th17 immune response may be modulated and inhibited by increasing IL-10 and/or decreasing TNF-α.

A. Inhibition of TNF-α Secretion Using an In Vitro Assay Platform of Dendritic Cells.

The inhibition assay for Th17 immune response is implemented by measuring TNF-α secretion after co-culture with the above-mentioned lactic acid bacteria. The assay procedures are listed as followings:
1. 200 mL human blood are obtained from healthy donors.
2. 1:1 blood isolates (Ficoll-paque) and blood are centrifuged at 400 g in 18-20° C. for 30-40 min.
3. Cells obtained from human PBMC (Peripheral Blood Mononuclear Cell) layer are washed with buffer solution 2-3 times and suspended with appropriate culture medium such as RPMI-1640.
4. CD14$^+$ monocytes are purified from PBMC cells by using CD14$^+$ microbeads (MiniMACS system).
5. Cells are differentiated into dendritic cells after incubating for 6-7 days by stimulating with IL-4 and GM-CSF and differentiated dendritic cells are then collected.
6. The lactic acid bacteria strain is activated 3 days before co-culture and is then heated for thermal death at 100° C. for 30 min.
7. The dendritic cells and the heated lactic acid bacteria strain (1:10) are co-cultured for 48 hours.
8. The supernatant of the cell culture medium is collected and used for measuring TNF-α amount by using ELISA (enzyme-linked-immunosorbent serologic assay).

The statistic results (Mean±SD) of data are analyzed in Table 3. Culture mixture having $10^6 \sim 10^8$ CFU of bacteria and $10^5 \sim 10^7$ cell human dendritic cells are co-cultured for 48 hours, and the supernatant of mixed culture medium are collected for measuring TNF-α amount in the supernatant by using ELISA. Here, a commercially available mixed culture product for anti-vaginitis, Biocan Vagi-guard®, having lactic acid bacteria for active ingredient is used as reference, LPS (Lipopolysaccharide) is used as positive control and background value contain cell only is used as negative control for detecting stimulated TNF-α concentration. As illustrated in the result, the experimental outcome of the present invention is significant in decreasing TNF-α secretion from human dendritic cells in comparison to positive control (LPS) and 84 fold and 135 fold lower than positive control (LPS) and reference (Biocan Vagi-guard®), respectively.

TABLE 3

TNF-α Secretion of human dendritic cells using LAB mixture of the present invention, control and reference

| Item | TNF-α Secretion (pg/mL) |
| --- | --- |
| Reference (Biocan Vagi-guard ®) | 2416 ± 81 |
| AP-32 + TE-33 + F-1 + CT-53 Mixture (gLac product) | 18 ± 15 |
| positive control (LPS) | 1521 ± 37 |
| Background (cell only) | 51 ± 44 |

B. Stimulation of IL-10 Secretion Using an In Vitro Assay Platform of Dendritic Cells.

In order to measure the increased amount of IL-10 secretion, human dendritic cells and the above-mentioned lactic acid bacteria are co-cultured and the secretion of IL-10 is then measured so as to determine the promoting effect on inhibiting inflammatory cells from secreting cytokine. The assay procedures are listed as followings:
1. 200 mL human blood are obtained from healthy donors;
2. 1:1 blood isolates (Ficoll-paque) and blood are centrifuged at 400 g in 18-20° C. for 30-40 min.
3. Cells obtained from human PBMC (Peripheral Blood Mononuclear Cell) layer are washed with buffer solution 2-3 times and suspended with appropriate culture medium such as RPMI-1640.
4. CD14$^+$ monocytes are purified from PBMC cells by using CD14$^+$ microbeads (MiniMACS system).
5. Cells are differentiated into dendritic cells after incubating for 6-7 days by stimulating with IL-4 and GM-CSF and differentiated dendritic cells are then collected.
6. The lactic acid bacteria strain is activated 3 days before co-culture and is then heated for thermal death at 100° C. for 30 min.
7. The dendritic cells and the heated lactic acid bacteria strain (1:10) are co-cultured for 48 hours.
8. The supernatant of the cell culture medium is collected and used for measuring IL-10 amount by using ELISA (enzyme-linked-immunosorbent serologic assay).

The statistic results (Mean±SD) of data are analyzed in Table 4. Culture mixture having $10^6 \sim 10^8$ CFU of bacteria and $10^5 \sim 10^7$ cell human dendritic cells are co-cultured for 48 hours, and the supernatant of mixed culture medium are collected for measuring IL-10 amount in the supernatant by using ELISA. Here, a background value contain cell only is used as negative control, a commercially available mixed culture product for anti-vaginitis, Biocan Vagi-guard®, having lactic acid bacteria for active ingredient is used as reference and PHA (Phytohemagglutinin) is used as positive control for detecting stimulated IL-10 concentration. As illustrated in the result, the experimental outcome of the present invention is significant in stimulating IL-10 secretion from human dendritic cells in comparison to negative control (Cell only) and 5 fold greater than reference (Biocan Vagi-guard®).

TABLE 4

IL-10 Secretion of human dendritic cells using LAB mixture of the present invention, control and reference

| Item | IL-10 Secretion (pg/mL) |
| --- | --- |
| Reference (Biocan Vagi-guard ®) | 900 ± 18 |
| AP-32 + TE-33 + F-1 + CT-53 mixture (gLac product) | 4941 ± 141 |
| Positive control (PHA) | 9145 ± 118 |
| Negative control (Cell only) | 241 ± 5 |

Resistance Assay of the Lactic Acid Bacteria of the Present Invention to Gastric Acid and Bile Salt One objective of the present invention is directed to new option other than drugs in treating vaginitis; therefore, identification for novel lactic acid bacteria which has no side effects against human and promotes health would be a new option for treating vaginitis To achieve anti-vaginitis capability, oral probiotic LAB strains need to be provided with specific capabilities, also resistant to human environment containing gastric acid and bile salt and resistant to generic drugs for treating vaginitis. Therefore, only LAB strain of the present invention that are provided with above-mentioned characteristics may be provided as medical applications for treating or alleviating vaginitis and used for lowering the recurrence thereof.

The LAB strains of the present invention are then tested for their resistance to gastric acid and bile salt to determine their capability for anti-inflammation in the intestinal tract. The assay procedures are listed as followings:

1. The LAB strains of the present invention are pre-activated for 3 days.
2. 1 mL LAB broth is sampled for counting original cell number, and the rest LAB is centrifuged at 500 g for 10 min and washed with de-ionized water for 2-3 times.
3. The LAB of the present invention is fully mixed with pH 2.5 medium adjusted by using HCl and placed in an incubator at 37° C.
4. 1 mL LAB both is sampled, washed with de-ionized water for 2-3 times and calculated for viable cell number each hour until the end of 3 hour incubation period.
5. The rest LAB broth is then centrifuged and the pellet is re-suspended with medium containing 1.5% (w/V) ox gall (Sigma) and fully mixed for incubation at 37° C.
6. 1 mL LAB both is sampled, washed with de-ionized water for 2-3 times and calculated for viable cell number each hour until the end of 4 hour incubation period.
7. The growth rate of LAB is recorded for calculating resistance to gastric acid and bile salt for LAB strains to determine if the growth of LAB strains of the present invention is inhibited in the presence of gastric acid and bile salt.

The tested results for gastric acid are analyzed and illustrated in Table 5 and FIG. 1. The results show that after activating with medium, treating with acidic buffering solution and bile salt, the cell number of AP-32, TE-33, F-1 and CT-53, the LAB strains of the present invention is not affected by treating gastric acid. The tested results for bile salt resistance are analyzed and illustrated in Table 6 and FIG. 1, where CT-53 are more sensitive to bile salt resulted in lowered cell number and the cell number of AP-32, TE-33 and F-1 strains is not affected by bile salt. Therefore, the above-mentioned results show that the LAB strains of the present invention may overcome obstacles due to the environment in human digesting system.

TABLE 5

Mix culture of LAB of the present invention with pH 2.5 HCl

| | Log CFU/mL | | | |
|---|---|---|---|---|
| Strain | Original cell number | pH 2.5-1 hr | pH 2.5-2 hr | pH 2.5-3 hr |
| AP-32 | 9.38 | 9.48 | 9.32 | 9.33 |
| TE-33 | 9.26 | 8.94 | 8.92 | 8.85 |
| F-1 | 9.37 | 9.15 | 9.34 | 9.11 |
| CT-53 | 9.41 | 9.29 | 9.19 | 9.28 |

TABLE 6

Mix culture of LAB of the present invention with 1.5% bile salt

| | Log CFU/mL | | | | |
|---|---|---|---|---|---|
| Strain | Original cell number | 1.5% bile salt-1 hr | 1.5% bile salt-2 hr | 1.5% bile salt-3 hr | 1.5% bile salt-4 hr |
| AP-32 | 9.38 | 9.02 | 8.87 | 7.95 | 7.21 |
| TE-33 | 9.26 | 8.63 | 8.05 | 8.17 | 8.07 |
| F-1 | 9.37 | 8.40 | 7.26 | 7.23 | 7.17 |
| CT-53 | 9.41 | 5.82 | 5.55 | 5.42 | 5.49 |

Figure 2:
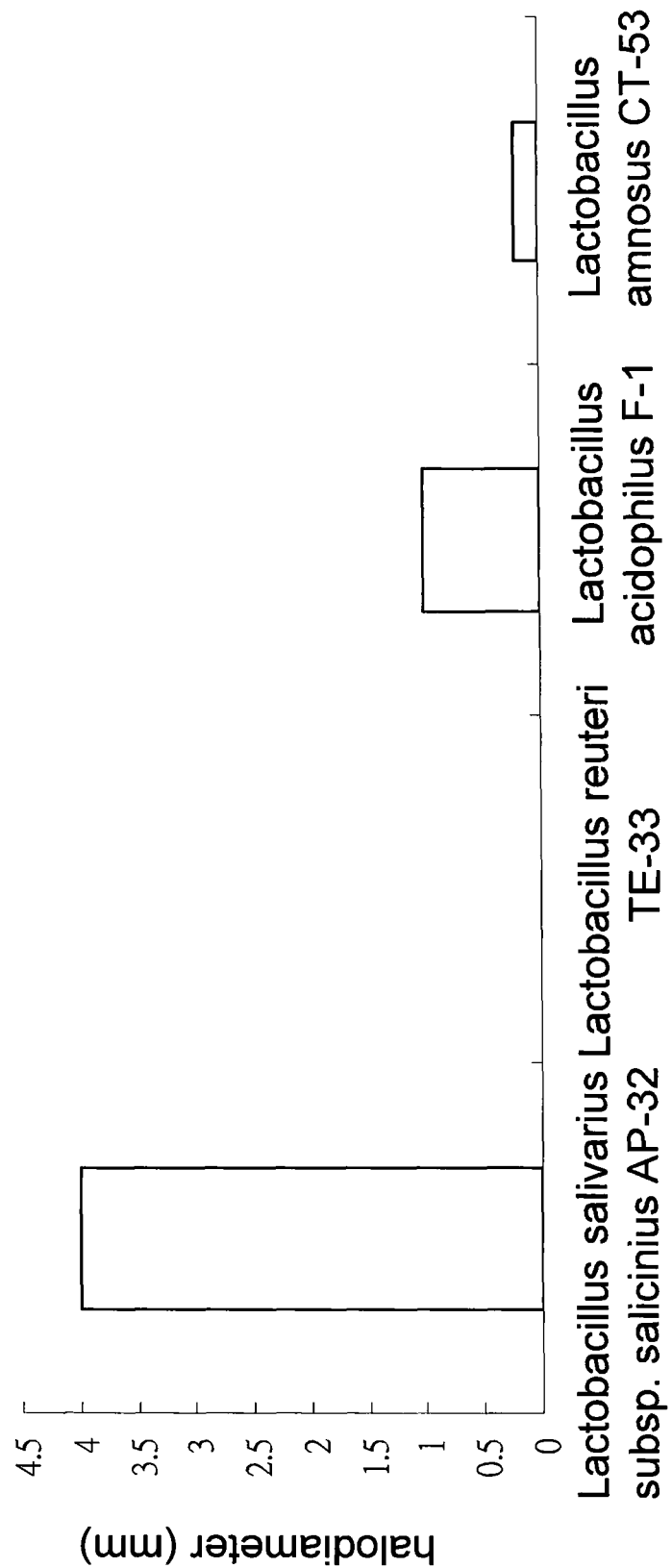
FIG. 2 is a block diagram schematically illustrating resistance to mold inhibitor, where all of *Lactobacillus salivarius* subsp. *salicinius* AP-32, *Lactobacillus reuteri* TE-33, *Lactobacillus acidophilus* F-1 and *Lactobacillus rhamnosus* CT-53 have inhibition zone diameter not greater than 4 mm and are strains having good resistance.

Resistance Assay of the Lactic Acid Bacteria of the Present Invention Against Clotrimazole, a Mold Inhibitor Commonly Used in Anti-Vaginitis Suppositories High density of LAB is seeded onto plate agar. Clotrimazole, a mold inhibitor, is dropped in the middle of plate. After incubation at 37° C. for 48 hours, the diameter size of inhibition zone is then observed to determine the resistance of LAB strains. For determining resistance, an inhibition zone having diameter not greater than 4 mm represents "resistance"; an inhibition zone having diameter between 4 and 5 mm represents "intermediate"; and an inhibition zone having diameter greater than 5 mm represents "susceptible". The resistance results are shown in Table 7 and FIG. 2, where AP-32, TE-33, F-1 and CT-53 are determined as strains with resistance.

TABLE 7

Resistance test of LAB of the present invention to a mold inhibitor Clotrimazole

| Strain Name | Inhibition zone diameter (mm) |
|---|---|
| AP-32 | 4 |
| TE-33 | 0 |
| F-1 | 1 |
| CT-53 | 0.2 |

To sum up, the composition containing LAB strains of the present invention have capabilities in inhibiting inflammation, resistance to bile salt, gastric acid and mold inhibitors and may be applied as oral probiotics. The above-mentioned composition may also be applied for anti-vaginitis so as to restrain pathogenic germ cluster and alleviate inflammatory symptoms such as redness, itching and pain and may be used in spray or tampon so as to promote women health.

While the invention can be subject to various modifications and alternative forms, a specific example thereof has been shown in the drawings and is herein described in detail. It should be understood, however, that the invention is not to be limited to the particular form disclosed, but on the contrary, the invention is to cover all modifications, equivalents, and alternatives falling within the spirit and scope of the appended claims.

What is claimed is:

1. An anti-inflammatory food composition, comprising:
a therapeutically effective amount of a biological pure culture of at least one *Lactobacillus* strain selected from the group consisting of *Lactobacillus salivarius* subsp. *salicinius* AP-32 (CCTCC stock No. M2011127), *Lactobacillus reuteri* TE-33 (CCTCC stock No. M2011126), *Lactobacillus acidophilus* F-1 (CCTCC stock No. M2011124), *Lactobacillus rhamnosus* CT-53 (CCTCC stock No. M2011129) and combinations thereof, wherein the *Lactobacillus* strain is resistant to bile salt, gastric acid and Clotrimazole; and a physiologically acceptable excipient or diluent.

2. The anti-inflammatory food composition as claimed in claim 1, wherein the *Lactobacillus* strain consists of *Lactobacillus salivarius* subsp. *salicinius* AP-32, *Lactobacillus reuteri* TE-33, *Lactobacillus acidophilus* F-1 and *Lactobacillus rhamnosus* CT-53.

3. The anti-inflammatory food composition as claimed in claim 1, wherein the excipient or diluent includes fermented milk, yogurt, cheese, milk beverage powder, tea, coffee or combinations thereof.

4. The anti-inflammatory food composition as claimed in claim 1, wherein the *Lactobacillus* strain is active or inactivated.

5. An anti-inflammatory pharmaceutical composition, comprising:

a therapeutically effective amount of a biological pure culture of at least one *Lactobacillus* strain selected from the group consisting of *Lactobacillus salivarius* subsp. *salicinius* AP-32 (CCTCC stock No. M2011127), *Lactobacillus reuteri* TE-33 (CCTCC stock No. M2011126), *Lactobacillus acidophilus* F-1 (CCTCC stock No. M2011124), *Lactobacillus rhamnosus* CT-53 (CCTCC stock No. M2011129) and combinations thereof, wherein the *Lactobacillus* strain is resistant to bile salt, gastric acid and Clotrimazole; and a pharmaceutically acceptable excipient or diluent.

6. The anti-inflammatory pharmaceutical composition as claimed in claim 5, wherein the *Lactobacillus* strain consists of *Lactobacillus salivarius* subsp. *salicinius* AP-32, *Lactobacillus reuteri* TE-33, *Lactobacillus acidophilus* F-1 and *Lactobacillus rhamnosus* CT-53.

7. The anti-inflammatory pharmaceutical composition as claimed in claim 5, wherein the *Lactobacillus* strain is active or inactivated.

8. The anti-inflammatory food composition as claimed in claim 1, wherein an inhibition zone diameter against Clotrimazole of the *Lactobacillus* strain is not greater than 4 mm.

9. The anti-inflammatory pharmaceutical composition as claimed in claim 5, wherein an inhibition zone diameter against Clotrimazole of the *Lactobacillus* strain is not greater than 4 mm.

10. A method for treating vaginitis comprising oral administration of a composition comprising a therapeutically effective amount of a biologically pure culture of at least one of *Lactobacillus salivarius* subsp. *salicinius* AP-32 (CCTCC stock No. M2011127), *Lactobacillus reuteri* TE-33 (CCTCC stock No. M2011126), *Lactobacillus acidophilus* F-1 (CCTCC stock No. M2011124), *Lactobacillus rhamnosus* CT-53 (CCTCC stock No. M2011129), wherein the biologically pure culture is resistant to bile salt, gastric acid and Clotrimazole, wherein the composition is a food composition or a pharmaceutical composition.

11. A biologically pure culture of a lactic acid bacteria strain selected from the group consisting of *Lactobacillus salivarius* subsp. *salicinius* AP-32 (CCTCC stock No. M2011127), *Lactobacillus reuteri* TE-33 (CCTCC stock No. M2011126), *Lactobacillus acidophilus* F-1 (CCTCC stock No. M2011124) and *Lactobacillus rhamnosus* CT-53 (CCTCC stock No. M2011129).

* * * * *